(12) United States Patent
Stampanoni et al.

(10) Patent No.: US 8,972,191 B2
(45) Date of Patent: Mar. 3, 2015

(54) LOW DOSE SINGLE STEP GRATING BASED X-RAY PHASE CONTRAST IMAGING

(75) Inventors: Marco Stampanoni, Endingen (CH); Ziyu Wu, Anhui (CN); Peiping Zhu, Beijing (CN)

(73) Assignees: Paul Scherrer Institut, Villigen, PSI (CH); Institut of High Energy Physics, Chinese Academy of Sciences, Beijing (CN)

( * ) Notice: Subject to any disclaimer, the term of this patent is extended or adjusted under 35 U.S.C. 154(b) by 852 days.

(21) Appl. No.: 13/148,198

(22) PCT Filed: Feb. 3, 2010

(86) PCT No.: PCT/EP2010/051291
§ 371 (c)(1),
(2), (4) Date: Oct. 13, 2011

(87) PCT Pub. No.: WO2010/089319
PCT Pub. Date: Aug. 12, 2010

(65) Prior Publication Data
US 2012/0041679 A1    Feb. 16, 2012

(30) Foreign Application Priority Data
Feb. 5, 2009   (EP) .................................... 09100099

(51) Int. Cl.
*G01B 9/02* (2006.01)
*G01N 21/31* (2006.01)
(Continued)

(52) U.S. Cl.
CPC *G01N 23/04* (2013.01); *A61B 6/00* (2013.01); *A61B 6/484* (2013.01); *A61B 6/4291* (2013.01)
USPC ................... 702/1; 702/81; 702/94; 702/127

(58) Field of Classification Search
USPC ................. 702/1, 81, 94, 127, 135, 150, 167; 250/394; 360/313; 378/36
See application file for complete search history.

(56) References Cited

U.S. PATENT DOCUMENTS

| 7,522,708 B2 | 4/2009 | Heismann et al. |
| 7,639,786 B2 | 12/2009 | Baumann et al. |

(Continued)

FOREIGN PATENT DOCUMENTS

| CN | 101011252 B | 12/2010 |
| CN | 101011253 B | 6/2011 |

(Continued)

OTHER PUBLICATIONS

Chen Bo et al.: "Theory and Method of X-ray Granting Phase Imaging", Journal of Physics, vol. 57, No. 3, pp. 1576-1581—English abstract on p. 1581.

*Primary Examiner* — Eliseo Ramos Feliciano
*Assistant Examiner* — Felix Suarez
(74) *Attorney, Agent, or Firm* — Laurence A. Greenberg; Werner H. Stemer; Ralph E. Locher

(57) ABSTRACT

Phase sensitive X-ray imaging methods provide substantially increased contrast over conventional absorption based imaging, and therefore new and otherwise inaccessible information. The use of gratings as optical elements in hard X-ray phase imaging overcomes some of the problems impairing the wider use of phase contrast in X-ray radiography and tomography. To separate the phase information from other contributions detected with a grating interferometer, a phase-stepping approach has been considered, which implies the acquisition of multiple radiographic projections. Here, an innovative, highly sensitive X-ray tomographic phase contrast imaging approach is presented based on grating interferometry, which extracts the phase contrast signal without the need of phase stepping. Compared to the existing phase step approach, the main advantage of this new method dubbed "reverse projection" is the significantly reduced delivered dose, without degradation of the image quality.

17 Claims, 5 Drawing Sheets

(51) Int. Cl.
*G06F 3/00* (2006.01)
*G06F 3/01* (2006.01)
*G01N 23/04* (2006.01)
*A61B 6/00* (2006.01)

(56) References Cited

U.S. PATENT DOCUMENTS

| | | | |
|---|---|---|---|
| 7,889,838 B2 * | 2/2011 | David et al. | 378/36 |
| 7,945,018 B2 | 5/2011 | Heismann et al. | |
| 7,949,095 B2 * | 5/2011 | Ning et al. | 378/62 |
| 8,041,004 B2 | 10/2011 | David et al. | |
| 2007/0183579 A1 | 8/2007 | Baumann et al. | |
| 2007/0183581 A1 | 8/2007 | Heismann et al. | |
| 2008/0186579 A1 | 8/2008 | Solak | |
| 2010/0296202 A1 * | 11/2010 | Boone et al. | 360/313 |
| 2010/0327175 A1 * | 12/2010 | Nesterets et al. | 250/393 |

FOREIGN PATENT DOCUMENTS

| | | |
|---|---|---|
| CN | 101257851 B | 6/2011 |
| CN | 101011250 B | 7/2011 |
| CN | 101011257 B | 7/2011 |
| CN | 101011254 B | 10/2011 |
| EP | 1 731 099 A1 | 12/2006 |
| JP | 2000098449 A | 4/2000 |
| JP | 2003135438 A | 5/2003 |
| JP | 2004203066 A | 8/2007 |
| JP | 2007203063 A | 8/2007 |
| JP | 2008517472 A | 5/2008 |
| JP | 2008545981 A | 12/2008 |
| WO | 2008006470 A1 | 1/2008 |

* cited by examiner

LOW DOSE SINGLE STEP GRATING BASED X-RAY PHASE CONTRAST IMAGING

BACKGROUND OF THE INVENTION

Field of the Invention

The present invention relates of a method and a system for low dose single step grating based X-ray phase contrast imaging.

It is well known that, differently from conventional visible light optics, the refractive index in X-ray optics is very close to and smaller than unity since the X-ray photon energy is often much larger than the atomic resonance energies. In first approximation, for small and negligible anisotropy in the medium, the index of refraction characterizing the optical properties of a tissue can be expressed—including X-ray absorption—with its complex form: $n=1-\delta-i\beta$ where $\delta$ is the decrement of the real part of the refractive index, characterizing the phase shifting property, while the imaginary part $\beta$ describes the absorption property of the sample. In conventional absorption-based radiography, the X-ray phase shift information is usually not directly utilized for image reconstruction. However, at photon energies greater than 10 keV and for light materials (made up of low-Z elements), the phase shift term plays a more prominent role than the attenuation term because $\delta$ is typically three orders of magnitude larger than $\beta$. As a consequence, phase-contrast modalities can generate significantly greater image contrast compared to conventional, absorption-based imaging. Furthermore, far from absorption edges, $\delta$ is inversely proportional to the square of the X-ray energy whilst $\beta$ decreases as the fourth power of energy. A significant consequence of this mechanism is that phase signals can be obtained with much lower dose deposition than absorption, a very important issue when radiation damage has to be taken into account such as in biological samples or in living systems.

Several approaches have been developed in order to record the phase signal. They can be classified as interferometric methods (with crystals), phase propagation methods, techniques based on an analyzer crystal or on grating interferometry.

In the prior art the feasibility of two-grating interferometry in the hard X-ray region using a pair of transmission gratings made by gold stripes on glass plates has been demonstrated. This work has since been extended to achieve a three-dimensional tomographic phase reconstruction using a hard X-ray two-gratings interferometer. Recently, three-grating interferometry in the hard X-ray region with low-brilliance tube-based X-ray sources has been demonstrated. This laboratory-based instrument is of great interest for applications in biology, medicine and for non-destructive testing. A grating interferometer setup is mechanically robust, is easy to align, has low sensitivity to mechanical drift and its requirements on temporal coherence ($\Delta E/E \sim 0.1$-$0.2$) and spatial coherence (few microns) are moderate: as a consequence the instrument can be easily scaled up to large fields of view, an important asset when used in combination with a conventional X-ray tube.

These characteristics make grating interferometry superior to other phase contrast approaches and set the pre-requisites for a broad use of phase contrast X-ray radiography and tomography.

To separate the phase information from other contributions, a phase-stepping approach is normally adopted. One of the gratings is displaced transversely to the incident beam whilst acquiring multiple projections. The intensity signal at each pixel in the detector plane oscillates as a function of the displacement and the phase of this intensity oscillation can be directly linked to the wave-front phase profile and to the decrement of the real part $\delta$ of the object's refractive index.

Obviously, this approach is loaded with the limitation of both (long) data acquisition time and severe dose released to specimen.

BRIEF SUMMARY OF THE INVENTION

It is therefore the objective of the present invention to provide a method and a system for the extraction of the phase information, which does not require a stepping procedure, thus overcoming limitations of both data acquisition time and dose imparted to the specimen.

This objective is achieved according to the present invention with respect to the system by an interferometer for x-rays, in particular hard x-rays, for obtaining quantitative x-ray images from a sample including:
a) an X-ray source;
b) a diffractive optical element, hereafter referred to as beam splitter grating, other than a Bragg crystal, preferably in transmission geometry;
c) a position-sensitive detector with spatially modulated detection sensitivity having a number of individual pixels;
d) means for recording the images of the detector;
e) means for evaluating the intensities for each pixel in a series of images in order to identify the characteristic of the object for each individual pixel as an absorption dominated pixel and/or a differential phase contrast dominated pixel and/or an x-ray scattering dominated pixel;
wherein the series of images is collected by continuously or stepwise rotating from 0 to $\pi$ or $2\pi$ either the sample or the interferometer and the source relative to the sample.

With respect to the method the objective is achieved according to the present invention by a method for obtaining quantitative x-ray images from a sample, comprising the steps of:
a) providing an X-ray source;
b) providing a diffractive optical element, hereafter referred to as beam splitter grating, other than a Bragg crystal, preferably in transmission geometry;
c) providing a position-sensitive detector with spatially modulated detection sensitivity having a number of individual pixels;
d) applying shots of the X-ray source to the probe and recording the images of the detector;
e) evaluating the intensities for each pixel in a series of images in order to identify the characteristic of the object for each individual pixel as an absorption dominated pixel and/or a differential phase contrast dominated pixel and/or an x-ray scattering dominated pixel;
wherein the series of images is collected by continuously or stepwise rotating from 0 to $2\pi$ either the sample or the interferometer relative to the sample.

The invented system and method therefore present an innovative, highly sensitive X-ray tomographic phase contrast imaging approach based on grating interferometry, which extracts the phase contrast signal without the need of phase stepping (PS). Compared to the existing phase step approach, the main advantage of this invention dubbed "reverse projection (RP)" is the significantly reduced delivered dose, without degradation of the image quality. The new technique sets the pre-requisites for future fast and low dose phase contrast imaging methods, fundamental for imaging biological specimens and in-vivo studies.

Typically, the beam splitter grating may be a line grating, preferably a phase grating; that is, a grating with low X-ray absorption, but considerable X-ray phase shift (Φ), the latter preferably of either $$\Phi \in \left((2l-1)\frac{\pi}{2} - \arcsin 0.8, \ (2l-1)\frac{\pi}{2} + \arcsin 0.8\right)$$

or $$\Phi \in ((2l-1)\pi - \arcsin 0.8, (2l-1)\pi + \arcsin 0.8), \text{ where } l=1, 2, 3 \ldots.$$

A further preferred embodiment of the present invention may provide the phase grating that acts as the beam splitter is made by deep etching into silicon, a polymer or similar material.

A further preferred embodiment of the present invention may provide the analyzer grating with one-dimensional grating structure being integrated into the detector, the pixel of the detector is in range of 2 to 10 times the size of the period of the grating, half lines with sensor in a pixel are sensitive to X-ray and half lines without sensor let X-ray go through. In this way the analyzer grating with 100% absorption can be achieved without needing to make heavy metal absorption gratings with high aspect ratio, in particular it is possible to avoid gold gratings.

A further preferred embodiment of the present invention may provide an analyzer grating having a one-dimensional grating structure with high X-ray absorption contrast, its period is the same as that of the self image of the phase grating, placed closely in front of the detector, with its lines parallel to those of the phase grating; preferably this analyzer grating serves as an anti-scatter grid, or an anti-scatter grid is used as a modulation mask.

Dimensioning the interferometer is fundamental for the present invention. Advantageously, the distance between the beam splitter grating and the analyzer grating is chosen to be an odd fractional Talbot distance, given by the equation $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda},$$

where n=1, 3, 5 ..., and $$\eta = \begin{cases} 1 & \text{if the phase shift of } G_1 \text{ is } (2l-1)\frac{\pi}{2}, \ p_2 = \frac{L + D_{n,sph}}{L} p_1 \\ 2 & \text{if the phase shift of } G_1 \text{ is } (2l-1)\pi, \ p_2 = \frac{L + D_{n,sph}}{L} \frac{p_1}{2} \end{cases},$$

where l=1, 2, 3 ..., $D_n$ is an odd fractional Talbot distance when the parallel X-ray beam is used, while $D_{n,sph}$ is that when the fan or cone X-ray beam is used, L is the distance between the source and the phase grating.

Further, the position of half slope on the shifting curve may be achieved by positioning at least one of the beam splitter grating and the analyzer grating relative to the probe in a direction substantially perpendicular to the orientation of the lines in at least one of the two gratings.

In order to establish a rather simple set-up of the present interferometer, a mechanism can be comprised to place the sample to be investigated between the source and the beam splitter grating or between the beam splitter grating and the analyzer grating being rotated from 0 to π or to 2π.

A further preferred embodiment of the present invention may provide a collimator placed between the source and the beam splitter grating limiting the spatial extent of the illuminating X-rays to a fan beam; a line-array detector is used, and a mechanism is comprised that allows to rotate (either stepwise or continuously) the sample relative to the rest of the apparatus, the rotational axis being perpendicular to the opening angle of the fan, and preferably at same time allows to translate (either stepwise or continuously) the sample relative to the rest of the apparatus along the direction parallel to the rotational axis.

Alternatively, a collimator placed between the source and the beam splitter grating may limit the spatial extent of the illuminating X-rays to a cone beam, a pixel-array detector is used, and a mechanism is comprised that allows to rotate the sample relative to the rest of the apparatus, perpendicular to the opening angle of the fan.

Excellent results with respect to the quality of the image can be achieved when an analysis procedure is implemented for reverse-projection data that comprises the steps of calculating, for each element of the detector, the absorption signal M and the refraction angle $\theta_r$ according to the following equations (8) and (9) resp.:

$$\ln\left(\frac{2S\left(\frac{x_g}{D}\right)I_o}{I(x_r, \phi, z) + I(-x_r, \phi + \pi, z)}\right) = M(x_r, \phi, z) = \int_{-\infty}^{\infty} \mu(x, y, z) dy_r \quad (8)$$

$$\frac{1}{C} \frac{I(x_r, \phi, z) - I(-x_r, \phi + \pi, z)}{(x_r, \phi, z) + I(-x_r, \phi + \pi, z)} = \theta_r(x_r, \phi, z) = -\int_{-\infty}^{\infty} \frac{\partial \delta(x, y, z)}{\partial x_r} dy_r \quad (9)$$

Preferred embodiments of the present invention are hereinafter described in more detail thereby referring to the attached drawings.

BRIEF DESCRIPTION OF THE DRAWINGS

FIG. 4(a) shows differential phase contrast radiography of a rat paw (7 stacks, RP-protocol).

DESCRIPTION OF THE INVENTION

Table 1 summarizes the experimental parameters for the tomographic scans of the three investigated samples: a rat brain (4% PFA, paraffin embedded), a (demineralized) mouse joint in PBS and a rat paw (4% PFA). All experiments have been performed at 25 keV and at the 3rd Talbot distance. Visibility of the interferometer was ~30%.

With reference to the above-mentioned figures, an innovative approach for the extraction of the phase information is presented which does not require a stepping procedure, thus overcoming limitations of both data acquisition time and dose released to specimens.

Figure 1:
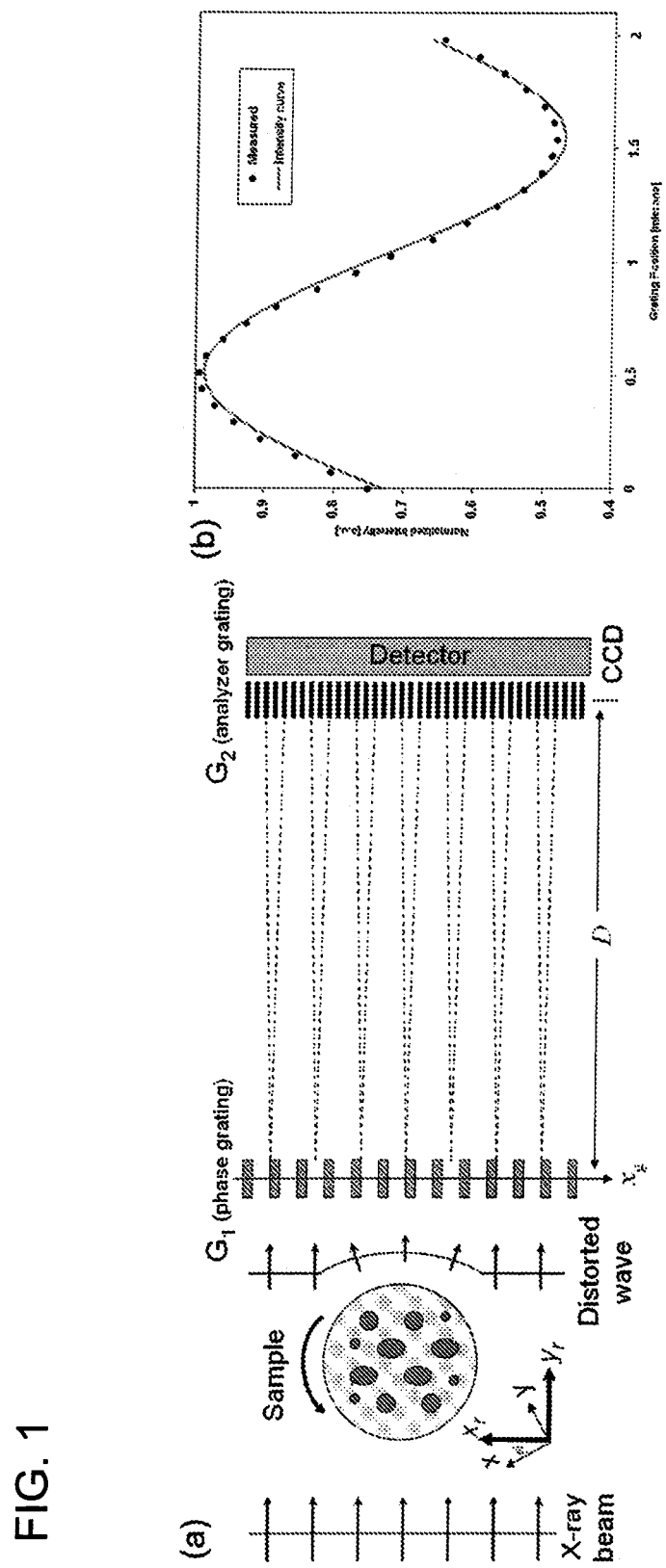
FIG. 1(a) shows the working principle of the grating interferometer: through the Talbot effect, a periodic interference pattern (known as self image) is formed behind the phase grating (G1), in the plane of the analyzer grating (G2).
FIG. 1(b) is a plot of the intensity oscillation (shifting curve) as a function of the grating position $x_g$ for a detector pixel over one period of the analyzer grating. The dots corresponds to the measured values (normalized to unit) while the gray line shows a sinusoidal fit.

This novel approach relies on the physical similarities between a crystal analyzer based system and a grating interferometer. Both techniques record refraction angle signals and, analogously to the rocking curve of a crystal analyzer, the properties of the shifting curve (see FIG. 1) can be exploited to fully describe the performance of a grating interferometer. The refraction angle, i.e., the phase information of the sample, can be extracted by setting the grating interferometer in the central position where the intensity curve follows a linear behavior.

According to the aforementioned analogy, the intensity I recorded by a detector positioned after the grating interferometer can be expressed as:

$$I = I_0 \cdot \exp\left[-\int_{-\infty}^{\infty} \mu(x, y, z) dy_r\right] \cdot S\left(\frac{x_g}{D} + \theta_r\right), \quad [1]$$

where $\mu$ is the linear absorption coefficient, $x_g$ denotes the relative displacement between the phase grating and the analyzer grating along the direction perpendicular to both the incoming beam and the line of gratings, $\theta_r$ is the refraction angle, D is the distance between the phase and the analyzer grating, $$S\left(\frac{x_g}{D}\right)$$

is the shifting curve. For the sake of simplicity, the scattering contribution—which would induce a weak increment of the background noise—is neglected. $(x_r, y_r, z)$ are the coordinates of the reference frame associated to the X-ray beam and (x,y,z) those associated with the sample. The two frames are linked by the rotation matrix $$\begin{pmatrix} x \\ y \end{pmatrix} = \begin{pmatrix} \cos\phi & -\sin\phi \\ \sin\phi & \cos\phi \end{pmatrix} \begin{pmatrix} x_r \\ y_r \end{pmatrix} \quad [2]$$

being $\phi$ the rotation angle between the $x_r$ and the x-axis around the z-axis.

With a good approximation, the behaviour of the shifting curve near its half slope may be considered linear so that, if $p_2$ is the period of the analyzer grating, $$\theta_r \leq \frac{p_2}{4D}$$

can be replaced by a first-order Taylor expansion. Further we can write:

$$S\left(\frac{x_g}{D} + \theta_r\right) = S\left(\frac{x_g}{D}\right) + \frac{dS\left(\frac{x_g}{D}\right)}{d\theta}\theta_r = S\left(\frac{x_g}{D}\right)(1 + C\theta_r) \quad [3]$$

where $$C = \frac{1}{S\left(\frac{x_g}{D}\right)} \frac{dS\left(\frac{x_g}{D}\right)}{d\theta}$$

is a constant.

The refraction angle in the X-Y plane (FIG. 1(a)) is determined by the line integral of the first-order derivative of the refractive index along the X-ray path and it may be written as:

$$\theta_r = -\int_{-\infty}^{\infty} \frac{\partial \delta}{\partial x_r} dy_r, \quad [4]$$

where $\delta$ corresponds to the decrement of the real part of the refractive index of the sample as mentioned in the introduction. Substituting Eqs. 3 and 4 into Eq. 1, the projected image for a grating interferometer can be described by:

$$I(x_r, z) = I_0 \exp\left\{-\int_{-\infty}^{\infty} \mu(x, y, z) dy_r\right\} S\left(\frac{x_g}{D}\right)\left[1 - C\int_{-\infty}^{\infty} \frac{\partial \delta(x, y, z)}{\partial x_r} dy_r\right] \quad [5]$$

$\mu$ is a scalar and therefore rotational-invariant, while $$\frac{\partial \delta}{\partial x_r}$$

strongly depends on the direction along which it is measured.

The projected image at the rotation angles $\phi$ and its corresponding reverse image at $\phi+\pi$ can be written as:

$$I(x_r, \phi, z) = \quad [6]$$
$$I_0 \exp\left\{-\int_{-\infty}^{\infty} \mu(x, y, z) dy_r\right\} S\left(\frac{x_g}{D}\right)\left[1 - C\int_{-\infty}^{\infty} \frac{\partial \delta(x, y, z)}{\partial x_r} dy_r\right]$$

-continued $$I(-x_r, \phi + \pi, z) = \quad [7]$$
$$I_0 \exp\left\{-\int_{-\infty}^{\infty} \mu(x, y, z) dy_r\right\} S\left(\frac{x_g}{D}\right)\left[1 + C \int_{-\infty}^{\infty} \frac{\partial \delta(x, y, z)}{\partial x_r} dy_r\right]$$

The absorption signal can be obtained from the two projected images by the sum of Eq. 6 and 7 and solving the Beer-Lambert relationship, i.e., $$\ln\left(\frac{2S\left(\frac{x_g}{D}\right)I_0}{I(x_r, \phi, z) + I(-x_r, \phi + \pi, z)}\right) = M(x_r, \phi, z) = \int_{-\infty}^{\infty} \mu(x, y, z) dy_r \quad [8]$$

In the same way, the angle of refraction can be obtained by a proper combination of Eq. 6 and 7, as shown in the following expression:

$$\frac{1}{C} \frac{I(x_r, \phi, z) - I(-x_r, \phi + \pi, z)}{I(x_r, \phi, z) + I(-x_r, \phi + \pi, z)} = \theta_r(x_r, \phi, z) = -\int_{-\infty}^{\infty} \frac{\partial \delta(x, y, z)}{\partial x_r} dy_r \quad [9]$$

According to fundamentals of computed tomography reconstruction, i.e., the Fourier Slice Theorem, the absorption coefficient as well as the refractive index can be easily obtained by the inverse Fourier Transform and a Hilbert filter:

$$\mu(x, y, z) = \quad [10]$$
$$\int_0^{\pi} d\phi \int_{-\infty}^{\infty} [M(x_r, \phi, z) * F^{-1}(|\rho|)] \cdot \delta(x\cos\phi + y\sin\phi - x_r) dx_r$$

$$\delta(x, y, z) = \quad [11]$$
$$-\int_0^{\pi} d\phi \int_{-\infty}^{\infty} \left[\theta_r(x_r, \phi, z) * F^{-1}\left(\frac{|\rho|}{2\pi j\rho}\right)\right] \cdot \delta(x\cos\phi + y\sin\phi - x_r) dx_r$$

where $\rho$ is the spatial frequency and $F^{-1}$ denotes the inverse Fourier transform.

Based on Eq. 10 and 11, we introduce here a novel acquisition protocol, dubbed "reverse projection" (RP) method.

It can be described in five steps:

(i) without sample, scan the phase grating or the analyzer grating along the transverse direction $x_g$ over one period of the analyzer grating and record the normalized intensity $$\frac{I}{I_0}$$

on the detector versus the angle $$\frac{x_g}{D},$$

i.e., get the shifting curve $$S\left(\frac{x_g}{D}\right),$$

(ii) set the grating interferometer at the center of the linear region of the shifting curve by positioning the phase grating or the analyzer grating at $x_g = p_2/4$ or $x_g = -p_2/4$, (iii) put the sample in front of or behind the phase grating, collect m angular projections of the sample over a rotation of 360°, (iv) extract M and $\theta_r$ according to Eq. 8 and Eq. 9 and finally (v) reconstruct either the absorption coefficient or the refractive index using the filtered back-projection. Therefore, the total number of acquired projection images is m.

On the contrary, the Phase Stepping (PS) acquisition protocol can be described in four steps:

(i) put the sample in front of or behind the phase grating, scan one of the two gratings along the transverse direction $x_g$ (k points over one period of the analyzer grating) and record one projection image at each point, (ii) repeat step (i) for a total of m/2 times over a sample rotation of 180°, (iii) extract the gradient signal via the Fourier analysis of the intensity signal and (iv) reconstruct the phase via a filtered back-projection.

For this second method, the total number of acquired projections images is k*m/2.

As a consequence, the total number of projections required by the RP protocol is reduced by a factor of k/2 compared to the PS.

The method was validated by performing both phase stepping (PS) and reverse projection (RP) experiments using the grating interferometer installed at the TOMCAT beamline of the Swiss Light Source at the Paul Scherrer Institute, Villigen, Switzerland. The energy was tuned at 25 keV and the interferometer was operated in the $3^{rd}$ Talbot distance. In this configuration, the visibility has been measured to be 30%. Additional details on the grating interferometer installed at TOMCAT can be found in public documentation related to this installation with the Paul Scherrer Institute.

In a first case study, we investigated two different samples: a rat brain first fixed in 4% paraformaldehyde (PFA) and then embedded in paraffin and a demineralized mouse joint, fixed only in a phosphate buffer solution (PBS) (no embedding). We used the mouse joint and the rat brain to test the reconstruction method both on small (<4 mm) and large (>10 mm) samples. Both specimens are weakly absorbing objects and therefore ideal candidates for phase contrast imaging. Reconstructions based on the two methods (PS and RP) are shown in FIGS. 2 and 3 while experimental parameters are summarized in Table 1.

Figure 2:
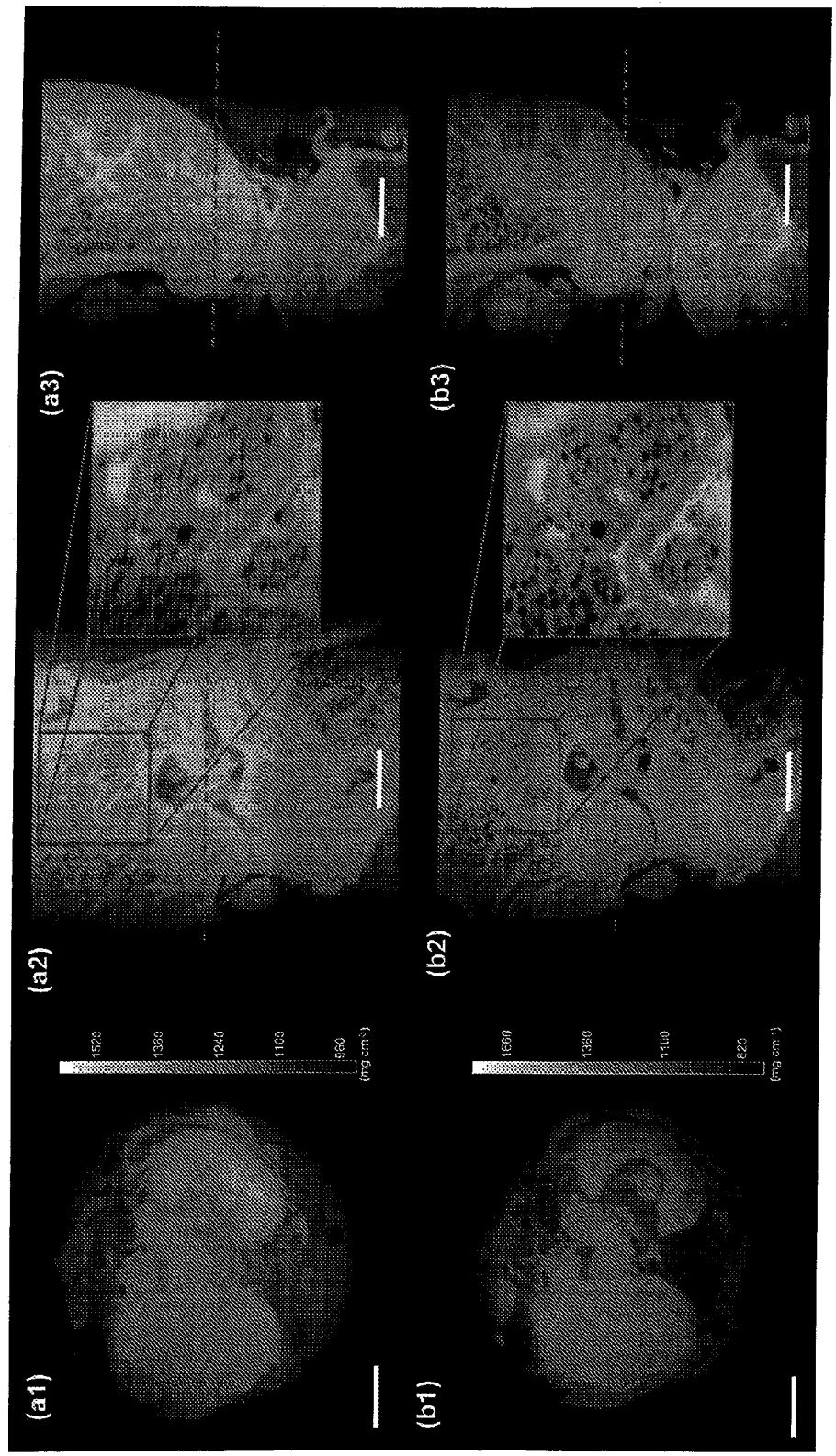
FIG. 2 illustrates phase contrast tomographic reconstructions of a demineralised mouse joint, acquired at a voxel size of 3.5×3.5×3.5 μm³. Sub-Figures a1 to a3 show the data obtained with the classical phase stepping (PS) protocol, while Sub-Figures b1 to b3 the reconstruction using the reverse projection (RP) method. a1 and b1 shows an axial slice: b1 is sharper than a1 and there are no ring artifacts (see text below). a2 and b2 depict a coronal slice through the joint, clearly showing that the RP protocol is less sensitive to typical horizontal stripes artifacts observed with the PS method (see enlarged inset). a3 and b3 show a sagittal view through the joint. The dotted lines mark the locations where the axial views (a1 and b1) have been taken. Scale bar is 500 microns.
Figure 3:
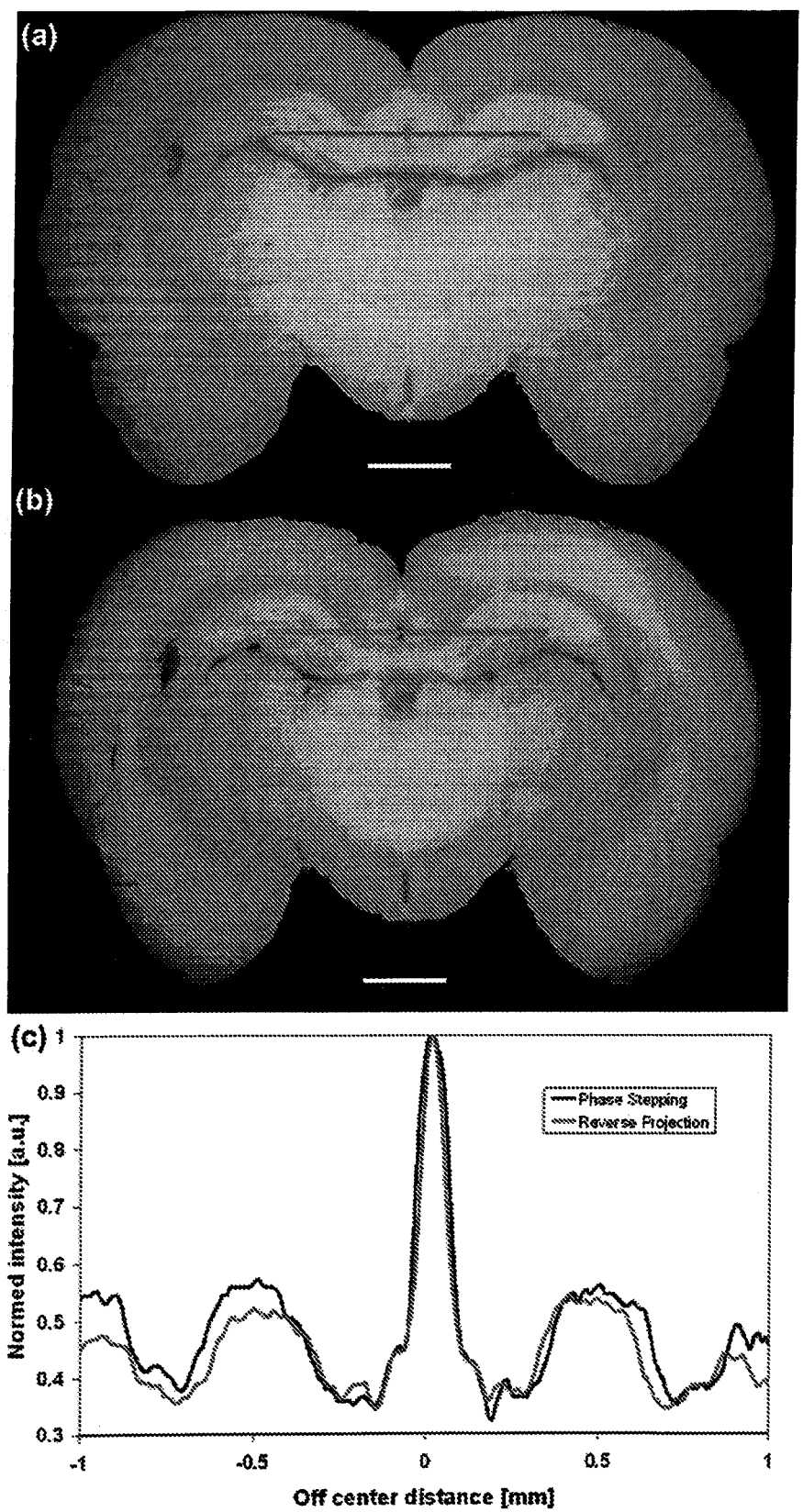
FIG. 3 represents a phase contrast reconstructed coronal slice of a rat brain, obtained after tomographic reconstruction using the PS- (a) and the RP-protocol (b). Qualitatively, both reconstructions are very similar. In (b) the effects of the grating imperfection (ring artifacts), as expected, are more evident. Figure (c) shows a quantitative comparison of two line profiles extracted at the position marked by colour bars (hippocampus region). Scale bar is 1 mm.

FIG. 2 shows axial, sagittal and coronal views of a mouse joint obtained with both PS and RP protocols (Table 1). The joint was immersed and fixed in an Eppendorf vial containing PBS to avoid any movements during the acquisition. A qualitative comparison of the images clearly shows that RP-reconstructions are comparable to those obtained with the PS approach. Moreover, looking at the inset shown in FIG. (2,a2) and (2,b2) the RP-slice appears to be sharper than the PS-reconstructions. This can be explained by the fact that the shifting curve is directly proportional to the refraction angle and that this—in the RP protocol—is obtained by simple subtraction of a reference image (with no sample) from the paired images described in Eq. 9. In addition, since with the RP method no phase-stepping is required, the system is less sensitive to mechanical instabilities.

The largest investigated sample, a rat brain, was mounted vertically on the flat surface of the sample support to match the horizontal field of view of the detector system. The vertical sample arrangement also enabled a direct reconstruction of coronal slices through the sample, an approach very useful when trying to identify anatomical brain regions (FIG. 3). The height of the sample was larger than the vertical height of the beam and therefore four scans have been collected along the vertical direction to image the whole brain. To achieve phase matching between sample and surroundings, we used an aquarium bath filled with room temperature liquid paraffin (chemical formula $C_nH_{2n+2}$ where n=5–17, density≈0.7 g cm$^{-3}$). For large samples too, a qualitative comparison of the images clearly shows that the RP-reconstruction is as good as the one obtained with the PS-approach. In addition, a line profile taken at the level of the hippocampus, see FIG. 3c, shows a quantitative good agreement between RP and PS approaches.

In the second case, the novel method has been validated using a more realistic sample, namely a specimen containing both soft and hard tissue. For this purpose, we investigated a rat paw (containing both bone and muscles) which was only fixed in 4% PFA. This fixation procedure is frequently used to maintain biological samples in a status as close as possible to their natural, original conditions. The rat paw was also mounted vertically in order to best match the horizontal field of view of the detector. Seven stacked scans were necessary to image the full sample volume.

Figure 4:
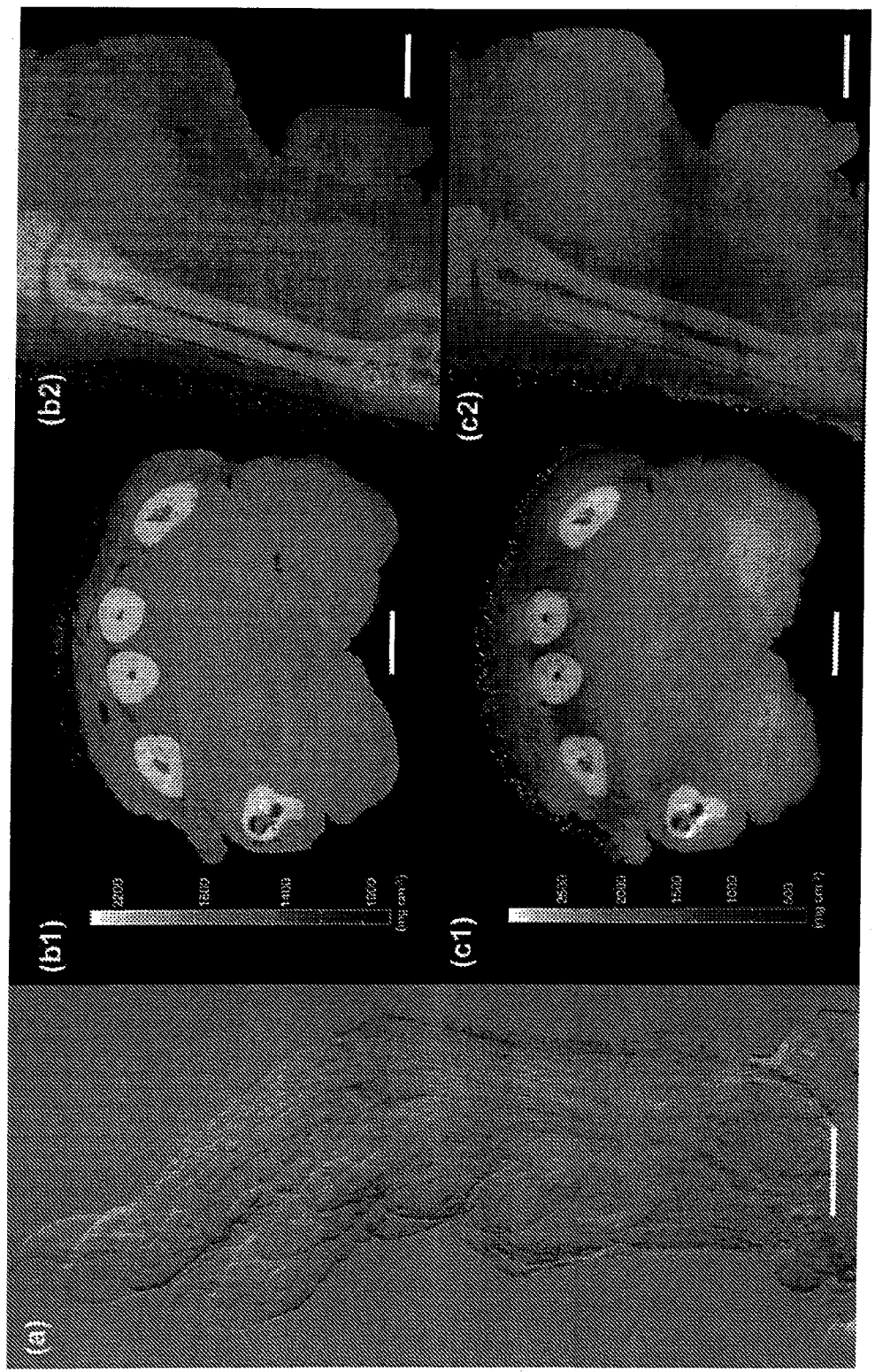
FIGS. 4(b1-2) and (c1-2) show axial and coronal slices through the paw acquired with the PS and RP protocol, respectively. Structural details of both soft (muscles, fat) and hard tissue (bone) are well visible. Scale bars are 2 mm in (a) and 1 mm for (b1-2) and (c1-2).

The measurement of the rat paw was the most challenging experiment since the sample has been measured in air. This usually causes large phase jumps at the air-specimen interface and explains the "star" artifacts visible in FIG. 4b-1 and, less serious, in 4c-1. This is because the shifting curve is saturated when $$\theta_r \geq \frac{p_2}{4D}$$

and, as a consequence, the RP method is not very sensitive to large refraction angles. This is not the case for the PS method, which has to cope with angles as large as $$\theta_r \leq \frac{p_2}{2D}.$$

Our invention introduces a novel approach for fast and low dose extraction of both the absorption coefficient and the refractive index of a sample using a grating interferometer is introduced. It is demonstrated that this new approach yields comparable information to the established phase stepping technique but with a reduction factor of k/2 in the total dose delivered to the sample. Moreover, the reverse projection approach makes high-sensitivity phase contrast computed tomography (CT) as straightforward as conventional, absorption based CT. It is first shown that this new method works well with parallel beam geometries but it is not difficult to generalize it to either cone or fan beam setups, making it accessible also to X-ray tube-based applications.

In particular, the significant decrease of the dose and the straight forward acquisition protocol does no affect image quality, while representing a major advancement in hard X-ray phase contrast tomography for synchrotron radiation and laboratory X-ray sources, enabling experiments impossible so far.

The next and probably most challenging application of the RP-protocol will be in-vivo phase contrast imaging. With the advent of new, high efficient and high speed detectors it will be possible to acquire the same amount of data within a fraction of a second. We estimate that it will be realistic to obtain a full tomographic data set with the RP protocol with a total exposure time of 2-3 seconds. This, together with the ongoing efforts regarding robust and reliable iterative reconstruction algorithms, requiring a significant smaller amount of projections, can push the total acquisition time below 1 s and hence opening up the possibility of phase contrast tomographic microscopy of small living animals.

Another very challenging application of the RP-protocol will be the quantitative 3D description of the scattering signal. This image contrast is generated by small-angle scattering within the sample and it provides complementary and otherwise inaccessible structural information at micrometer and sub-micrometer length scale. However, the signal is not rotational-invariant and therefore it will be very challenging to quantitatively obtain such information in 3D.

Further developments will concern the manufacturing of optimized gratings for high X-ray energies leading to the implementation of the RP-protocol in new medical X-ray CT scanners that would offer a significant increase in soft tissue sensitivity, a characteristic now provided (at much lower resolutions however) only by much more expensive techniques such as magnetic resonance imaging.

Finally, we would like to point out that this approach is not limited to X-ray imaging and may be easily generalized to other methods such as grating based neutron phase imaging and visible light differential interference contrast (DIC) microscopy where a similar shifting curve is considered and a quantitative phase description appears possible.

TABLE 1

|  | Mouse joint | | Rat brain | | Rat paw | |
| --- | --- | --- | --- | --- | --- | --- |
|  | Phase Stepping | Reverse Projection | Phase Stepping | Reverse Projection | Phase Stepping | Reverse Projection |
| Rotation | 0-180° | 0-360° | 0-180° | 0-360° | 0-180° | 0-360° |
| Pixel size [μm] | 3.5 × 3.5 | 3.5 × 3.5 | 11.2 × 11.2 | 11.2 × 11.2 | 7.4 × 7.4 | 7.4 × 7.4 |
| Field of view [mm] | 3.58 × 3.58 | 3.58 × 3.58 | 11.45 × 3.6[1] | 11.45 × 3.6 | 15.5 × 3.6 | 15.5 × 3.6 |
| Angl. proj. | 181 | 361 | 361 | 721 | 501 | 1001 |
| Phase steps | 9 | 1 | 9 | 1 | 9 | 1 |
| Single exposure [ms] | 200 | 200 | 200 | 200 | 60 | 60 |

TABLE 1-continued

| | Mouse joint | | Rat brain | | Rat paw | |
|---|---|---|---|---|---|---|
| | Phase Stepping | Reverse Projection | Phase Stepping | Reverse Projection | Phase Stepping | Reverse Projection |
| Total exposure (s) | 325 | 72 | 650 | 144 | 270 | 60 |

[1] The optical system always produces field of views with a square shape. However, along the vertical direction the size of the field of view is reduced and limited by the vertical size of the beam (approximately 3.6 mm at 25 keV and at 25 m from the source for the TOMCAT beamline of the Swiss Light Source).

Supplementary Material I

Ring-like artefacts due to grating imperfections are discussed hereinafter.

A careful study of the reconstructed images reveals that the reverse projections (RP) protocol imposes more stringent requirements on gratings, i.e., it needs better full-field uniformity and lower local grating imperfections than gratings suitable for the phase stepping (PS) method. In particular, imperfections may induce small ring-like artifacts in the RP-reconstructed slices, which are less evident or missing in PS-reconstructions.

Figure 5:
FIG. 5(a1-2) is a tomographic reconstruction of a rat brain—(a1-2) obtained with the PS protocol, (b1-2) obtained with the RP-protocol using Eq. 11 to calculate the map of the index of refraction. Scale bar is 1 mm in (a1,b1) and 2 mm in (a2,b2).

Ring artifacts are clearly visible in FIG. 5, for both coronal (b1) and sagittal (b2) cuts. Due to the averaging effect associated to the phase stepping extraction, the PS-protocol is significantly less sensitive to grating defects and therefore the rings artifact are less pronounced, see FIG. 5a1-2.

The invention claimed is:

1. An imaging set-up for reverse projection to obtain quantitative X-ray images from a sample and to quantitatively extract both absorption and phase information from the sample, the imaging set-up comprising:
   an X-ray source generating an X-ray beam;
   gratings including a beam splitter grating and an analyzer grating having their respective lines parallel to each other, said beam splitter grating being a phase grating and said analyzer grating is a line absorption grating with high X-ray absorption;
   a mechanism for placing the sample to be investigated either between said X-ray source and the said beam splitter grating or between said beam splitter grating and said analyzer grating;
   a position-sensitive detector with spatially modulated detection sensitivity having a number of individual pixels;
   means for recording images of said position-sensitive detector, a series of M images is collected by continuously or stepwise rotating from zero (0) to pi ($\pi$) or 2pi ($2\pi$) either the sample or said gratings and said X-ray source relative to the sample, wherein each image taken at an angle $0 \leq \phi \leq \pi$ contains a corresponding reverse projection image taken at an angle $\pi \leq \phi + \pi \leq 2\pi$, yielding in total a number of M/2 pairs of specular images;
   means for calculating pixel-wise an absorption image M and an refraction angle $\theta_r$ image out of the pairs of specular images without a need for phase stepping according to:

$$M(x_r, \phi, z) = \int_{-\infty}^{\infty} \mu(x, y, z) dy_r = \ln\left(\frac{2S\left(\frac{x_g}{D}\right)I_0}{I(x_r, \phi, z) + I(-x_r, \phi + \pi, z)}\right)$$

$$\theta_r(x_r, \phi, z) = -\int_{-\infty}^{\infty} \frac{\partial \delta(x, y, z)}{\partial x_r} dy_r = \frac{1}{C} \frac{I(x_r, \phi, z) - I(-x_r, \phi + \pi, z)}{I(x_r, \phi, z) + I(-x_r, \phi + \pi, z)}$$

where:
(x, y, z) are first spatial coordinates associated with the sample;
($x_r$, $y_r$, z) are second spatial coordinates associated to the X-ray beam, the first and second coordinates being linked by a rotation matrix:

$$\begin{pmatrix} x \\ y \end{pmatrix} = \begin{pmatrix} \cos\phi & -\sin\phi \\ \sin\phi & \cos\phi \end{pmatrix} \begin{pmatrix} x_r \\ y_r \end{pmatrix},$$

where $\phi$ is a rotation angle between $x_r$ axis and x axis around a z axis;
$I_o$ is an incident X-ray intensity;
$I(x_r, \phi, z)$ is intensity recorded at said position-sensitive detector for a beam decided by $x_r$, z and the rotation angle $\phi$;
$x_g$ denotes a relative displacement between said phase grating and said analyzer grating along a direction perpendicular to both an incoming beam and a line of said gratings;
D is a distance between said phase grating and said analyzer grating;

$$S\left(\frac{x_g}{D}\right)$$

is a shifting curve;
C is a constant; and
$M(x_r, \phi, z)$ and $\theta_r(x_r, \phi, z)$ are inline definitions representing an absorption signal and a refraction angle, respectively, for a given coordinate $x_r$, z, and the rotation angle $\phi$.

2. The imaging setup according to claim 1, wherein the intensity I recorded by said position-sensitive detector is expressed as:

$$I = I_0 \cdot \exp\left[-\int_{-\infty}^{\infty} \mu(x, y, z) dy_r\right] \cdot S\left(\frac{x_g}{D} + \theta_r\right)$$

where $\mu(x, y, z)$ is a linear absorption coefficient at the spatial coordinate (x, y, z), $x_g$ denotes the relative displacement between said phase grating and said analyzer grating along the direction perpendicular to both the incoming beam and the line of said gratings, $\theta_r$ is the refraction angle, D is the distance between said phase grating and said analyzer grating, $$S\left(\frac{x_g}{D}\right)$$

is the shifting curve.

3. The imaging set-up according to claim 1, wherein said analyzer grating has a one-dimensional grating structure with high X-ray absorption contrast and is placed in front of said position sensitive detector with its lines parallel to those of said beam splitter grating.

4. The imaging set-up according to claim 1, wherein said analyzer grating has a one-dimensional grating structure with high X-ray absorption contrast, its period is a same as that of a self image of said beam splitter grating, is placed in front of said position sensitive detector with its lines parallel to those of said beam splitter grating.

5. The imaging set-up according to claim 1, wherein a distance between said beam splitter grating and said analyzer grating is chosen to be an odd fractional Talbot distance, given by equation $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda},$$

where n=1, 3, 5 . . . , and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases},$$

where l=1, 2, 3 . . . $D_n$ is the odd fractional Talbot distance when a parallel X-ray beam is used, while $D_{n,sph}$ is that when a fan or cone X-ray beam is used, L is a distance between said x-ray source and said phase grating, and $p_1$ and $p_2$ represent a period of said beam splitter grating and said analyzer grating, respectively.

6. The imaging set-up according to claim 1, wherein said beam splitter grating is a line phase grating with low X-ray absorption, but with considerable X-ray phase shift Φ, the X-ray phase shift defined as either $$\Phi \in \left((2l-1)\frac{\pi}{2} - \arcsin 0.8, (2l-1)\frac{\pi}{2} + \arcsin 0.8\right)$$

or

Φ∈((2l−1)π−arcsin 0.8, (2l−1)π+arcsin 0.8), where l=1, 2, 3 . . . .

7. The imaging set-up according to claim 1, wherein said beam splitter grating is a line phase grating with low X-ray absorption and made from a material selected from the group consisting of silicon and a polymer.

8. The imaging set-up according to claim 1, wherein said analyzer grating is either placed front of said position sensitive detector or with its one-dimensional grating structure integrated into said position sensitive detector, a pixel of said position sensitive detector is from 2 to 10 times a size of a period of said analyzer grating, half lines with sensor in a pixel are sensitive to X-ray and half lines without sensor let X-ray go through.

9. The imaging set-up according to claim 1, further comprising a collimator disposed between said X-ray source and said beam splitter grating, said collimator limiting a spatial extent of illuminating X-rays to a fan beam, a line-array detector is used, and said mechanism rotates stepwise or continuously the sample relative to a rest of the apparatus, a rotational axis being perpendicular to an opening angle of a fan, and at a same time allows to translate either stepwise or continuously the sample relative to the rest of the apparatus along a direction parallel to a rotational axis.

10. A method for reverse projection to obtain quantitative X-ray images from a sample and to quantitatively extract both absorption and phase information from the sample, which comprises the steps of:
 providing an X-ray source;
 providing gratings including a beam splitter grating and an analyzer grating having their respective lines parallel to each other, wherein the beam splitter grating is a line grating selected from the group consisting of an absorption grating with high X-ray absorption and a phase grating with low X-ray absorption, and the analyzer grating is a line absorption grating with high X-ray absorption;
 providing a position-sensitive detector with spatially modulated detection sensitivity having a number of individual pixels;
 positioning at least one of the gratings relative to a probe in a direction $x_g$ being substantially perpendicular to both an incoming beam and an orientation of the lines of grating to make an imaging set-up on a center of a linear region of a shifting curve $$S\left(\frac{x_g}{D}\right);$$

placing the sample to be investigated either between the X-ray source and the beam splitter grating or between the beam splitter grating and the analyzer grating, applying shots of the X-ray source to the sample and recording the images of the position-sensitive detector;
 recording the images of the position-sensitive detector, wherein a series of M images is collected by continuously or stepwise rotating from zero (0) to pi (π) or 2pi (2π) either the sample or the gratings and the X-ray source relative to the sample, wherein each image taken at an angle 0≤Φ≤π contains a corresponding reverse projection image taken at an angle π≤Φ+π≤2π, yielding in total a number of M/2 pairs of specular images; and
 means for calculating pixel-wise an absorption image M and an refraction angle $θ_r$ image out of the pairs of specular images without a need for phase stepping according to:

$$M(x_r, \phi, z) = \int_{-\infty}^{\infty} \mu(x, y, z) dy_r = \ln\left(\frac{2S\left(\frac{x_g}{D}\right)I_0}{I(x_r, \phi, z) + I(-x_r, \phi + \pi, z)}\right)$$

$$\theta_r(x_r, \phi, z) = -\int_{-\infty}^{\infty} \frac{\partial \delta(x, y, z)}{\partial x_r} dy_r = \frac{1}{C} \frac{I(x_r, \phi, z) - I(-x_r, \phi + \pi, z)}{I(x_r, \phi, z) + I(-x_r, \phi + \pi, z)}$$

where:
 (x, y, z) are first spatial coordinates associated with the sample;
 ($x_r$, $y_r$, z) are second spatial coordinates associated to the X-ray beam, the first and second coordinates being linked by a rotation matrix:

$$\begin{pmatrix} x \\ y \end{pmatrix} = \begin{pmatrix} \cos\phi & -\sin\phi \\ \sin\phi & \cos\phi \end{pmatrix} \begin{pmatrix} x_r \\ y_r \end{pmatrix},$$

where $\phi$ is a rotation angle between $x_r$ axis and x axis around a z axis;

$I_o$ is an incident X-ray intensity;

$I(x_r, \phi, z)$ is intensity recorded at said position-sensitive detector for a beam decided by $x_r, z$ and the rotation angle $\phi$;

D is a distance between said phase grating and said analyzer grating;

C is a constant; and $M(x_r, \phi, z)$ and $\theta_r(x_r, \phi, z)$ are inline definitions representing an absorption signal and a refraction angle, respectively, for a given coordinate $x_r$, z, and the rotation angle $\phi$.

11. The method according to claim 10, wherein if the beam splitter grating is a line phase grating with low X-ray absorption, a thickness of a grating line will be with considerable X-ray phase shift $\Phi$, the X-ray phase shift being either $$\Phi \in \left( (2l-1)\frac{\pi}{2} - \arcsin 0.8, (2l-1)\frac{\pi}{2} + \arcsin 0.8 \right)$$

or $\Phi \in ((2l-1)\pi - \arcsin 0.8, (2l-1)\pi + \arcsin 0.8)$, where $l=1, 2, 3 \ldots$.

12. The method according to claim 10, wherein if the beam splitter grating is a line phase grating with low X-ray absorption, it will be made from a material selected from the group consisting of silicon and polymer.

13. The method according to claim 10, wherein the analyzer grating has a one-dimensional grating structure with high X-ray absorption contrast, its period is a same as that of the image of the beam splitter grating, and is placed in front of the position-sensitive detector with its lines parallel to those of the phase grating, the one-dimensional grating structure serving as an anti-scatter grid, or an anti-scatter grid is used as a modulation mask.

14. The method according to claim 10, wherein a distance between the beam splitter grating and the analyzer grating is chosen to be an odd fractional Talbot distance, given by equation $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda},$$

where $n=1, 3, 5 \ldots$, and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases},$$

where $l=1, 2, 3 \ldots$.

$D_n$ is the odd fractional Talbot distance when a parallel X-ray beam is used, while $D_{n,sph}$ is that when a fan or cone X-ray beam is used, L is a distance between the X-ray source and the phase grating, and $p_1$ and $p_2$ represent a period of the beam splitter grating and the analyzer grating, respectively.

15. The method according to claim 10, which further comprises disposing a collimator between the X-ray source and the beam splitter grating for limiting a spatial extent of illuminating X-rays to a fan beam, a line-array detector is used, and a mechanism is comprised that allows to rotate either stepwise or continuously the sample relative to the rest of the apparatus, the rotational axis being perpendicular to an opening angle of the fan, and at a same time allows to translate either stepwise or continuously the sample relative to the rest of the apparatus along a direction parallel to a rotational axis.

16. The method according to claim 10, which further comprises disposing a collimator between the x-ray source and the beam splitter grating for limiting a spatial extent of illuminating X-rays to a cone beam, a pixel-array detector is used, and a mechanism is comprised that allows to rotate the sample relative to the rest of the apparatus, perpendicular to an opening angle of the fan.

17. The method according to claim 10, which further comprises disposing the analyzer grating either in front of the position-sensitive detector or with its one-dimensional grating structure integrated into the position-sensitive detector, the pixel of the detector is from 2 to 10 times the size of the period of the grating, half lines with sensor in a pixel are sensitive to X-ray and half lines without sensor let X-ray go through.

* * * * *